(12) United States Patent
Chaudhari et al.

(10) Patent No.: US 8,865,219 B2
(45) Date of Patent: Oct. 21, 2014

(54) ORODISPERSIBLE TABLETS OF BITTER ACTIVE PRINCIPLES

(75) Inventors: Mahendra B. Chaudhari, Maharashtra (IN); Edouard Gendrot, Garnay (FR)

(73) Assignee: Ethypharm (FR)

( * ) Notice: Subject to any disclaimer, the term of this patent is extended or adjusted under 35 U.S.C. 154(b) by 777 days.

(21) Appl. No.: 12/088,205

(22) PCT Filed: Sep. 25, 2006

(86) PCT No.: PCT/FR2006/002185
§ 371 (c)(1),
(2), (4) Date: Mar. 26, 2008

(87) PCT Pub. No.: WO2007/036632
PCT Pub. Date: Apr. 5, 2007

(65) Prior Publication Data
US 2008/0248111 A1  Oct. 9, 2008

(30) Foreign Application Priority Data
Sep. 28, 2005  (FR) ..................................... 05 09900

(51) Int. Cl.
*A61K 9/16* (2006.01)
*A61K 9/26* (2006.01)
*A61P 25/24* (2006.01)
*C07C 211/55* (2006.01)
*A61K 9/20* (2006.01)
*A61K 9/50* (2006.01)

(52) U.S. Cl.
CPC ... *A61K 9/16* (2013.01); *A61K 9/20* (2013.01); *A61K 9/1635* (2013.01); *A61K 9/2077* (2013.01); *A61K 9/5026* (2013.01)
USPC ........... 424/496; 424/464; 424/469; 424/470; 424/489; 424/490; 514/17.6; 514/17.5; 564/317; 564/316; 564/315; 564/305

(58) Field of Classification Search
None
See application file for complete search history.

(56) References Cited

U.S. PATENT DOCUMENTS

| 3,594,470 | A | | 7/1971 | Borodkin et al. |
| 4,855,287 | A | * | 8/1989 | Watanabe et al. ............... 514/41 |
| 5,219,563 | A | | 6/1993 | Douglas et al. |
| 7,867,517 | B2 | * | 1/2011 | Massironi ..................... 424/484 |
| 2005/0036977 | A1 | * | 2/2005 | Gole et al. .................... 424/76.1 |
| 2005/0147663 | A1 | * | 7/2005 | Mohan et al. ................. 424/451 |
| 2005/0181050 | A1 | * | 8/2005 | Hirsh et al. ................... 424/469 |
| 2005/0250838 | A1 | * | 11/2005 | Challapalli et al. ........... 514/419 |

FOREIGN PATENT DOCUMENTS

| EP | 0693281 A2 | | 1/1996 | |
| JP | 8040884 A | | 2/1996 | |
| WO | 9944580 A1 | | 9/1999 | |
| WO | 0040224 A1 | | 7/2000 | |
| WO | WO 00/40224 | * | 7/2000 | ............. A61K 9/50 |
| WO | WO 01/80826 | * | 11/2001 | ............. A61K 9/00 |
| WO | WO 03/002101 | * | 1/2003 | ............. A61K 9/48 |
| WO | 2004091585 A1 | | 10/2004 | |

OTHER PUBLICATIONS

International Search Report for PCT/FR2006/002185.
Office Action dated Mar. 6, 2012 of corresponding Japanese application.

* cited by examiner

*Primary Examiner* — Jeffrey T Palenik
(74) *Attorney, Agent, or Firm* — Caesar, Rivise, Bernstein, Cohen & Pokotilow, Ltd.

(57) ABSTRACT

The invention concerns coated granules including (A) at least one amine-containing pharmacological active principle, preferably as an acid addition salt, the pharmacological active principle being complexed by low cation-exchange resin containing carboxylic acid groups (COO"), and (B) at least 15 wt. %, based on the total weight of the active principle/low cation-exchange resin complex, of at least one hydrophilic adsorbent, the mixture of the components (A) and (B) being coated with a gastrosoluble polymer. The invention also concerns a method for preparing such granules, as well as orodispesible tablets containing such granules.

14 Claims, No Drawings

ORODISPERSIBLE TABLETS OF BITTER ACTIVE PRINCIPLES

BACKGROUND

The present invention relates to coated granules containing pharmacological active principles whose unpleasant gustatory properties are masked both by complexation by a cation-exchange resin and by coating. It also relates to orodispersible tablets containing such coated granules.

It is known to complex pharmacologically active substances that have disagreeable gustatory qualities, such as a bitter taste, by combining them with cation-exchange resins. Thus, U.S. Pat. No. 6,193,962, U.S. Pat. No. 5,811,436 and U.S. Pat. No. 6,514,492; disclose liquid pharmaceutical formulations that contain active principles complexed by a crosslinked polymethacrylic acid resin, in suspension in an aqueous phase. U.S. Pat. No. 5,219,563 discloses uncoated dry granules of a bitter active principle (ranitidine) complexed by crosslinked polymethacrylic acid.

In the context of its research aiming to develop orodispersible tablets of active substances for which it is necessary to mask the unpleasant taste, the applicant has however observed that, for a certain number of substances that are particularly bitter and/or that leave a burning sensation in the mouth, such as fluoxetine, the simple masking of the taste by complexing with a cation-exchange resin was insufficient.

It is furthermore widely known in the art to mask the unpleasant taste of certain active principles by coating with gastrosoluble polymers. In the case of substances such as fluoxetine that have a very pronounced bitter flavor and leave a burning sensation in the mouth, such masking by coating is however relatively ineffective and requires polymer amounts that are too large. Thus, the coating of fluoxetine with 50 wt % of polymer is barely enough to mask the bitterness of the molecule and amounts ranging beyond this value do not make it possible to obtain dissolution kinetics in an acid medium that conforms to the specifications of the USP monograph for fluoxetine tablets which requires a dissolution rate greater than 85 wt % in 15 minutes in a 0.1 N HCl solution.

There is therefore still a need for orodispersible tablets of pharmacologically active substances that have particularly unpleasant gustatory qualities, which combine both good taste masking and rapid release of the active principle in an acid medium.

SUMMARY OF THE INVENTION

The applicant has observed, with surprise, that it was possible to prepare pharmaceutical formulations of active principles that are very bitter and/or that cause a burning sensation in the oral mucous membrane, which make it possible to effectively mask the taste of the active principle and dissolve rapidly in acid medium, by complexing, in a known manner, the active principle with a weak cation-exchange resin comprising carboxylic acid groups and by carrying out the granulation of the complex thus obtained in the presence of at least 15 wt %, relative to the resin/active principle complex, of at least one hydrophilic adsorbent, before subjecting the granules thus obtained to coating with a gastrosoluble polymer.

Consequently, one subject of the present invention is coated granules formed by a core comprising a mixture:
 (A) of at least one aminated pharmacological active principle preferably in the form of an acid addition salt, said pharmacological active principle being complexed by a weak cation-exchange resin comprising carboxylic acid groups (COO$^-$); and
 (B) of at least 15% by weight, relative to the total weight of the active principle/weak cation-exchange resin complex, of at least one hydrophilic adsorbent,
said core comprising the mixture of components (A) and (B) being coated by a gastrosoluble polymer.

Another subject of the invention is orodispersible tablets comprising such coated granules and one or more adjuvants chosen from disintegrants, diluents, excipients for direct compression, flow agents, lubricants, sweeteners and flavors.

DETAILED DESCRIPTION OF PREFERRED EMBODIMENTS

The active principle which may be formulated in the form of granules and orodispersible tablets according to the present invention may, in principle, be any water-soluble pharmacologically active molecule which comprises an amine functional group enabling the formation of ionic bonds with the carboxyl groups of the cation-exchange resin. It is, of course, preferably an active principle which, during ingestion, has unpleasant gustatory qualities that require effective masking. As explained in the introduction, the invention is of particular interest for active principles that are very bitter and/or that leave a burning sensation in the oral mucous membrane, such as fluoxetine, risperidone and most antibiotics, for which the known taste masking methods are insufficient or unsuitable.

The active principle is generally used in the form of an acid addition salt which has a better solubility in water than the unprotonated form, this solubility being essential for the complexing step of the active principle by the cation-exchange resin which is generally carried out in an aqueous phase. In principle, it is possible to use any salt resulting from the addition of a known pharmacologically acceptable acid. One preferred acid is hydrochloric acid.

The cation-exchange resin is a weak cation-exchange resin comprising —COO$^-$ functional groups. Such a resin has the advantage of effectively retaining the active principle complexed at a weakly basic, neutral or weakly acidic pH (pH of saliva: 7±0.5), but of rapidly releasing it in a strongly acidic medium where the high concentration of protons displaces the dissociation equilibrium of the cation-exchange resin toward the protonation of the carboxyl sites.

These cation-exchange resins are crosslinked so as to be insoluble in all solvents, including water, and at all pH values. They are not absorbed by a man, which makes them non-toxic excipients. The cation-exchange resins used in the present invention preferably have an ion-exchange capacity at least equal to 5 mEq/g, preferably at least equal to 10 mEq/g and in particular between 10 and 30 mEq/g.

Mention may be made, as examples of preferred weak cation-exchange resins, of methacrylic acid/divinylbenzene copolymers, sold for example under the name AMBERLITE® IRP88 by Röhm and Haas and under the name INDION 234 by Indion Resins.

In order to obtain effective masking of the taste of the active principle, the cation-exchange resin is preferably used in a weight amount at least equal to that of the active principle, and in particular in a weight amount greater than that of the active principle. Active principle/resin weight ratios between 1 and 4, preferably between 1.5 and 2.5 have given satisfactory results. The preparation of the active principle/cation-exchange resin complex will be described in detail below and will be illustrated in the examples.

As indicated above, the granulation of the active principle/cation-exchange resin complex must be carried out in the presence of a relatively large amount, at least equal to 15% by weight relative to the total weight of the active principle/weak cation-exchange resin complex, of at least one hydrophilic adsorbent. This large amount of hydrophilic adsorbent allows, on the one hand, the excess water at the end of the complexing step to be adsorbed and allows the use of such an active principle/weak cation-exchange resin complex in a dry formulation such as a tablet, and promotes the rapid dissolution of the complexed active principle in acid medium, despite the double protection, by complexing and coating, which normally has a tendency to hinder the release of the active principle.

Preferably, in the case of fluoxetine, the presence of hydrophilic adsorbent, in an amount at least equal to 15% by weight relative to the total weight of the active principle/weak cation-exchange resin complex, makes it possible to obtain dissolution kinetics in acid medium that conform to the specifications of the USP monograph for fluoxetine tablets which requires a dissolution rate greater than 85 wt % in 15 minutes in a 0.1 N HCl solution.

It is possible to use any hydrophilic adsorbent or any combination of hydrophilic adsorbents generally used for granulation, such as cellulose derivatives, in particular microcrystalline cellulose, starches, lactose, in particular lactose monohydrate, polyols and colloidal silica such as Aerosil, preferably precipitated silica such as SYLOID 244 FP). In one preferred embodiment of the granules according to the invention, these granules contain from 15 to 50% by weight, relative to the total weight of the active principle/weak cation-exchange resin complex, and in particular from 20 to 40% by weight, of at least one hydrophilic adsorbent.

In one preferred embodiment, the combination of a microcrystalline cellulose and a colloidal silica is used as hydrophilic agents.

In one particularly preferred embodiment of the invention, the active principle/cation-exchange resin complex is granulated in the presence of at least 15 wt % of microcrystalline cellulose and at least 5 wt % of colloidal silica.

The granules obtained, containing both the active principle/weak cation-exchange resin complex and at least 15% by weight, relative to the total weight of the active principle/cation-exchange resin complex, of at least one hydrophilic adsorbent, are coated by one or more gastrosoluble polymers in a sufficient amount to effectively mask the taste of possible active principle residues that are not complexed by the cation-exchange resin.

The expression "gastrosoluble polymer" is understood according to the present invention to mean any polymer that is insoluble in a basic or neutral aqueous medium and which, when it is brought into contact with the acidic medium of the stomach that generally has a pH between 1 and 3, completely dissolves in the latter.

The gastrosoluble polymers are known and may be chosen, for example, from cellulose derivatives and (meth)acrylic polymers. As examples of suitable cellulose derivatives, ethyl cellulose, hydroxypropylmethyl cellulose and hydroxypropyl cellulose can be mentioned. The (meth)acrylic polymers that can be used as gastrosoluble polymers for coating the granules are, for example, EUDRAGIT E 100 (alkyl methacrylate/aminoalkyl methacrylate copolymers).

The amount of gastrosoluble polymer necessary for obtaining satisfactory masking of the residue taste is generally between 5 and 50%, preferably between 10 and 40% and in particular between 15 and 30% by weight, relative to the total weight of the granules before coating. The coating may be carried out according to known techniques, for example by spraying an aqueous and/or alcoholic solution of the polymer onto the granules suspended in a fluidized bed.

A final subject of the invention is a process for manufacturing coated granules comprising:
(a) the complexation, in aqueous medium, of at least one aminated pharmacological active principle by a weak cation-exchange resin comprising carboxyl groups (—COO⁻);
(b) the granulation of the active principle/resin complex obtained still containing at least some of the water used for the complexation, in the presence of at least 15% by weight, preferably 15 to 50% by weight, relative to the total weight of the active principle/resin complex, of at least one hydrophilic adsorbent; and
(c) the coating of the granules obtained in step (b) by at least one gastrosoluble polymer.

The complexation of the active principle or principles by the cation-exchange resin is carried out by simple contacting of these two components in an aqueous medium with stirring. It is generally and preferably carried out by first dispersing the active principle in the aqueous medium in order to at least partially dissolve it. The cation-exchange resin is then added in one go or in several portions and the whole assembly is stirred for a sufficient time to obtain the complexation of almost all of the active principle. The complexation process is relatively slow as the dissolved active principle must penetrate into the insoluble resin particles that are swollen by the aqueous solvent. The mixture stirring time required to obtain complexation of almost all of the active principle is generally at least equal to 1 hour, preferably between 2 and 4 hours. In the case of the complexation of fluoxetine by a crosslinked polymethacrylic acid resin, the applicant has observed that after 2 hours, 98% of the active principle had been complexed by the resin. Mouth taste tests have however shown that it was preferable to prolong the complexing time to 3 hours. In an alternative embodiment of the process of the invention, the complexation could be carried out in two steps: a first step of complexation with a fraction of the resin, then filtration of the suspension and contacting of the remaining fraction of resin with the filtrate containing a low concentration of active principle that is not yet complexed.

At the end of the complexation step, the active principle/resin complex is not dried but is subjected to the following granulation step with at least some of the water used for the complexation step. Some of the complexation water, generally between 30 and 70%, is removed by a suitable technique such as filtration, settling, sedimentation by centrifuging or hydroextraction, or by a combination of these techniques. The applicant has especially developed a technique for hydroextraction of the complex by centrifuging in a filtration bag (see example 1) which makes it possible to remove around 50 wt % of the water and which is considerably faster than the method of settling followed by suction of the supernatant used to date.

The hydrophilic adsorbent or adsorbents are then mixed with the still wet complex and the whole assembly is granulated according to a known process.

Coating of the granules thus obtained may also be carried out by any suitable known technique, for example by spraying a solution of the gastrosoluble polymer, optionally with the addition of one or more adjuvants, onto the granules suspended in a fluidized bed.

The preparation of an orodispersible tablet according to the invention from granules obtained in the manner described above is carried out in a known manner (see, for example, French patent applications FR2679451, FR2766086, FR2785538, FR2790387, FR2831820 by the applicant) by mixing the coated granules described above with one or more known adjuvants, chosen, for example, from disintegrants, diluents, preferably soluble diluents such as sugars or polyols, excipients for direct compression, flow agents, lubricants, sweeteners and flavors, and dry tabletting in a tablet press.

The invention is illustrated below using the following exemplary embodiments.

Example 1

Preparation of Orodispersible Tablets of Fluoxetine

Complexation (Step (a) of the Process)

100 g of fluoxetine hydrochloride and 200 g of AMBERLITE IRP88 resin (polymethacrylic acid crosslinked by divinylbenzene) were weighed, then screened (630 µm screen). 800 g of purified water was stirred then the fluoxetine was slowly introduced therein over a period of around 5 minutes and the mixture continued to be stirred for around 5 minutes, before gradually adding, over a period of around 10 minutes, the AMBERLITE IRP88. A thickening of the suspension was then observed which refluidified however quite rapidly. The mixture thus obtained continued to be stirred for 2 hours while taking care to limit the stirring speed to the minimum value tolerated by the stirrer in order to avoid the formation of bubbles.

Hydroextraction of the Complex Formed

The mixture obtained in step (a) above was poured into a polypropylene filtration bag (porosity: 1-5 µm) placed in a basket of a centrifugal separator (Rousselet RC 20 centrifugal separator) that was rotated at a speed of 400 rpm. The filtrate, which was a cloudy and off-white suspension of very fine particles, was recovered and it was again poured into the filtration bag containing the retentant. This recycling of the filtrate was carried out twice, with an increase of the speed of the centrifugal separator of between 500 and 1000 rpm between each recycling step. After the last recycling step of the filtrate, the centrifugal separator was rotated for a few minutes. The centrifuging was stopped when the filtrate was recovered at a rate of 1 drop per second. Thus a retentant was obtained from which around 53% of the water initially used had been eliminated. This still wet retentant was used directly for the granulation step.

Granulation (Step (b) of the Process)

Over a period of around 5 minutes, 48 g of microcrystalline cellulose (AVICEL PH 101) and 18 g of precipitated silica (SYLOID 244 FP) which had been screened were added to the centrifuged fluoxetine/cation-exchange resin complex introduced previously into a Kenwood "Chef" mixer rotating at the minimum speed. After around 5 to 10 minutes, the mixture was dried in a fluidized bed (GPCG 1) until it had a residual degree of moisture of around 5%. The powder obtained was hygroscopic and composed of relatively fine particles. It was screened (500 µm) before being coated.

Coating (Step (c) of the Process)

165 g of EUDRAGIT E100 were added to 1287 g of 96% ethanol and they were stirred until the polymer had completely dissolved, then 18 g of precipitated silica (SYLOID 244 FP) were added with stirring.

Two batches of granules obtained under identical conditions in the manner described above were transferred into the coating chamber of a GPCG 1 fluidized bed equipped with a Wurster coater and the coating solution was sprayed with a nozzle through the bottom onto the fluidized mass. The spraying pressure was set at a relatively low value in order to prevent the powder from blocking the spray nozzle.

Preparation of the Orodispersible Tablets 400 mg orodispersible tablets containing a dose of 20 mg of fluoxetine base were prepared by dry compression. These tablets had the following composition:

| Ingredient | wt % |
|---|---|
| Fluoxetine (hydrochloride) | 5.59 |
| Weak cation-exchange resin (AMBERLITE IRP88) | 4.61 |
| Microcrystalline cellulose (AVICEL PH 101) | 2.68 |
| Precipitated silica | 2.51 |
| EUDRAGIT E100 | 4.61 |
| TOTAL coated granules | 26.57 |
| Mannitol powder (MANNITOL 60) | 17.75 |
| Granulated mannitol (PEARLITOL SD200) | 41.18 |
| Crospovidone (KOLLIDON CL) | 8.00 |
| Aspartame | 4.00 |
| Spearmint flavor | 4.00 |
| Magnesium stearate | 1.50 |
| TOTAL | 100 |

The crospovidone, aspartame, precipitated silica, flavor and mannitol powder were weighed then screened through a 1000 µm manual screen. The granulated mannitol was also screened through this same screen but kept in a separate container. The crospovidone, aspartame, precipitated silica, flavor and powdered mannitol were mixed and the fluoxetine granules, then the granulated mannitol, were added to the mixture. The whole assembly was mixed in a cubic mixer by rotating for 10 minutes at 14 rpm. Next, the magnesium stearate, previously screened through a 630 µm screen, was added. The mixture was mixed again for 2 minutes at 14 rpm.

Tabletting conditions:
Punch: 11 mm polo;
Mass: 400 mg;
Hardness: 40 N;
Thickness: around 4 mm;
Production rate: 10 000-15 000 tablets/h; and
Fill-o-matic regime=10 rpm.

The disintegration time of the tablets thus prepared, determined by a test on 6 tablets, was between 15 and 17 seconds. These tablets meet the specifications of the USP monograph for fluoxetine tablets that requires a dissolution rate greater than 85 wt % in 15 minutes in a 0.1 N HCl solution.

Mouth taste tests carried out did not reveal any bitterness or burning sensation in the oral mucous membrane.

Example 2

Orodispersible Tablets of Risperidone 80 g of cation-exchange resin (INDION 204) were dispersed in 200 g of purified water and were stirred with a helical stirrer for 10 minutes until a suspension was obtained that was free of lumps. 20 g of risperidone were added and the mixture was stirred for 1 hour at ambient temperature. The risperidone/resin complex obtained was granulated with a mixture of 278 g of lactose monohydrate and 22 g of colloidal silica (AEROSIL 200) in a planetary mixer. The granulation mass was dried in a fluidized bed until it had a degree of moisture of 1 to 3%. After screening through a 40 mesh screen, the granules were coated with an aqueous coating solution, prepared from 41.0 g of EUDRAGIT EPO, 2.88 g of sodium lauryl sulfate, 6.15 g of dibutyl sebacate and 255 g of purified water, in a fluidized bed by the bottom-spray technique. The granules obtained were dried in the same fluidized bed until they had a moisture content between 5 and 7%, then they were screened through a 35 mesh screen.

400 mg orodispersible tablets containing a dose of 4 mg of risperidone, having the following composition, were prepared in a similar manner to that described in example 1.

| Ingredient | wt % |
| --- | --- |
| Coated risperidone/resin granules | 22.5 |
| Mannitol powder (MANNITOL 60) | 21.5 |
| Granulated mannitol (PEARLITOL SD200) | 40.5 |
| POLYPLASDONE XL | 10.0 |
| Aspartame | 2.0 |
| AEROSIL 200 | 0.5 |
| Mint flavor | 1.0 |
| Magnesium stearate | 2.50 |
| TOTAL | 100 |

The tablets had a disintegration time in the oral cavity of less than 40 seconds. During mouth taste tests, they did not have the slightest bitter taste nor did they cause a burning sensation in the oral cavity.

The invention claimed is:

1. A coated granule formed by coating a granule with a coating comprising a gastrosoluble polymer, said granule being formed by granulating a mixture comprising:
   (A) fluoxetine or acid addition salts thereof, said fluoxetine being complexed by a weak cation-exchange resin comprising carboxylic acid groups (COO$^-$); and
   (B) a hydrophilic adsorbent comprising at least 15% by weight, relative to the total weight of the complex, of microcrystalline cellulose and at least 5% by weight, relative to the total weight of the complex, of colloidal silica;
   wherein said coated granule masks the taste of the fluoxetine; and
   wherein said coated granule has dissolution kinetics in acid medium that conform to the specification of the USP monograph for fluoxetine tablets.

2. The coated granule as claimed in claim 1, wherein the hydrophilic adsorbent (B) is present in an amount of 20% to 50% by weight relative to the total weight of the complex.

3. The coated granule as claimed in claim 1, wherein the acid addition salts are hydrochlorides.

4. The coated granule as claimed in claim 1, wherein the weak cation-exchange resin is a crosslinked polymethacrylic acid.

5. An orodispersible tablet comprising coated granules and one or more adjuvants selected from the group consisting of disintegrants, diluents, and excipients for direct compression, flow agents, lubricants, sweeteners and flavors, wherein said coated granules are formed by coating the granules with a coating comprising a gastrosoluble polymer, and wherein said granules are formed by granulating a mixture comprising:
   (A) fluoxetine or acid addition salts thereof, said fluoxetine being complexed by a weak cation-exchange resin comprising carboxylic acid groups (COO$^-$); and
   (B) a hydrophilic adsorbent comprising at least 15% by weight, relative to the total weight of the complex, of microcrystalline cellulose and at least 5% by weight, relative to the total weight of the complex, of colloidal silica;
   wherein said coated granule masks the taste of the fluoxetine; and
   wherein said coated granule has dissolution kinetics in acid medium that conform to the specification of the USP monograph for fluoxetine tablets.

6. A process for manufacturing coated granules as claimed in claim 1, comprising:
   (a) complexing at least one aminated pharmacological active principle selected from the group consisting of fluoxetine and addition salts thereof, with a weak cation-exchange resin comprising carboxyl groups (COO$^-$), in an aqueous medium, to provide an active principle/resin complex;
   (b) granulating the active principle/resin complex which still contains at least some water used for complexing, in the presence of a hydrophilic adsorbent comprising at least 15% by weight, relative to the total weight of the complex, of microcrystalline cellulose and at least 5% by weight, relative to the total weight of the complex, of colloidal silica; and
   (c) coating the granules formed in step (b) with at least one gastrosoluble polymer to provide the coated granules.

7. The process of claim 6, wherein the granulating is conducted in the presence of 20% to 50% by weight, relative to the total weight of the active principle/resin complex, of the hydrophilic adsorbent.

8. The coated granule as claimed in claim 1, wherein the hydrophilic adsorbent (B) is present in an amount of 20 to 40%, relative to the total weight of the complex.

9. The coated granule as claimed in claim 1, wherein the weak cation-exchange resin is adapted to retain the fluoxetine complexed thereto at a pH of 6.5 to 7.5, and to release the fluoxetine in a more acidic medium.

10. The coated granule as claimed in claim 1, wherein a weight ratio of said fluoxetine to said cation-exchange resin is between 1 and 4.

11. The coated granule as claimed in claim 10, wherein a weight ratio of said fluoxetine to said cation-exchange resin is between 1.5 and 2.5.

12. The orodispersible tablet as claimed in claim 5, wherein the hydrophilic adsorbent (B) is present in an amount of 20% to 50% by weight, relative to the total weight of the complex.

13. The coated granule as claimed in claim 5, wherein the acid addition salts are hydrochlorides.

14. The coated granule as claimed in claim 5, wherein the weak cation-exchange resin is a crosslinked polymethacrylic acid.

* * * * *